(12) United States Patent
Soltis et al.

(10) Patent No.: US 7,890,174 B2
(45) Date of Patent: Feb. 15, 2011

(54) MEDICAL ELECTRICAL LEAD WITH DEPLOYABLE FIXATION FEATURES

(75) Inventors: Brian D. Soltis, St. Paul, MN (US); Bruce A. Tockman, Scandia, MN (US); Kent C. B. Stalker, San Marcos, CA (US); Eric T. Johnson, Temecula, CA (US); Peter J. D'Aquanni, Murrieta, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1260 days.

(21) Appl. No.: 11/421,990

(22) Filed: Jun. 2, 2006

(65) Prior Publication Data

US 2007/0282412 A1 Dec. 6, 2007

(51) Int. Cl.
*A61N 1/36* (2006.01)
(52) U.S. Cl. .......................................... 607/37; 606/41
(58) Field of Classification Search ........................ None
See application file for complete search history.

(56) References Cited

U.S. PATENT DOCUMENTS

| | | | |
|---|---|---|---|
| 4,072,154 A * | 2/1978 | Anderson et al. ............. 607/37 |
| 4,401,120 A | 8/1983 | Hartlaub et al. | |
| 5,545,206 A | 8/1996 | Carson | |
| 6,445,958 B1 | 9/2002 | Machek et al. | |
| 6,697,676 B2 | 2/2004 | Dahl et al. | |
| 6,976,987 B2 | 12/2005 | Flores | |
| 2002/0165533 A1* | 11/2002 | Flores ........................ 606/41 |
| 2003/0097128 A1 | 5/2003 | Hayzelden | |
| 2003/0109852 A1 | 6/2003 | Peterson et al. | |
| 2003/0114844 A1 | 6/2003 | Ormsby et al. | |
| 2003/0181855 A1 | 9/2003 | Simpson et al. | |

FOREIGN PATENT DOCUMENTS

WO 03084433 10/2003

OTHER PUBLICATIONS

International Search Report and Written Opinion of international application No. PCT/US2007/067885, mailed Jan. 29, 2008, 15 pp.

* cited by examiner

*Primary Examiner*—Carl H. Layno
*Assistant Examiner*—Jon-Eric Morales
(74) *Attorney, Agent, or Firm*—Faegre & Benson LLP

(57) ABSTRACT

A medical electrical lead adapted to be at least partially implanted in a cardiac vessel includes a fixation feature operable to change from an undeployed configuration to a deployed configuration in which the fixation feature is adapted to engage an inner surface of the cardiac vessel. A tendon is disposed within a lumen of the lead and is operatively connected to the fixation feature and adapted to cause the fixation feature to change from the undeployed configuration to the deployed configuration for acute and/or chronic fixation of the lead. In one embodiment, the fixation feature includes a deflectable region of the lead which in the deployed configuration causes a surface of the lead body to engage the inner surface of the cardiac vessel. In another embodiment, the fixation feature includes a radially expandable structure for engaging the inner surface of the vessel in the deployed configuration.

11 Claims, 12 Drawing Sheets

MEDICAL ELECTRICAL LEAD WITH DEPLOYABLE FIXATION FEATURES

CROSS-REFERENCE TO RELATED APPLICATIONS

The present application is related to co-pending U.S. patent application Ser. No. 11/422,000 entitled "MEDICAL ELECTRICAL LEAD WITH EXPANDABLE FIXATION FEATURES" and filed Jun. 2, 2009. The above-identified application is incorporated herein by reference for all purposes.

TECHNICAL FIELD

The present invention relates to devices and methods for fixation of medical electrical leads. Specifically, the present invention is directed to deployable devices and methods for acute and chronic fixation of a portion of a medical electrical lead within a patient's vasculature, and in particular, the coronary vasculature.

BACKGROUND

Implantable medical devices for treating irregular contractions of the heart with electrical stimuli are known. Exemplary implantable devices are defibrillators and pacemakers. Various types of electrical leads for defibrillators and pacemakers have been suggested, many of which are placed transvenously. Such leads are introduced into the patient's vasculature at a venous access site and travel through veins to the sites where the leads' electrodes will be implanted or otherwise contact target coronary tissue. Electrodes for transvenously-placed leads can be implanted in the endocardium (the tissue lining the inside of the heart) of the right atrium or ventricle, or alternatively, in the branch vessels of the coronary venous system. In particular, lead electrodes can be implanted in the coronary sinus or a branch vessel thereof for sensing and/or stimulation of the left side of the heart (i.e., the left ventricle).

Various techniques have been used to facilitate fixation of the foregoing types of leads at the desired implantation sites. For leads partially implanted within the coronary venous system, fixation techniques should provide fixation sufficient to secure the lead in the desired implanted position, both acutely and chronically, without impeding delivery of the lead to the implantation site.

There is thus a need in the art for a device and method for fixation of cardiac leads within the coronary vasculature which does not interfere with delivery of the lead and which can be deployed after delivery to provide acute and/or chronic fixation.

SUMMARY

The present invention, in one embodiment, is an implantable system comprising a pulse generator, and a lead having a proximal end coupled to the pulse generator. The lead is configured to be partially implanted in a cardiac vessel and includes an elongate lead body defining a proximal region and a distal region, the distal region including an electrode on the body, a deflection location on the body, and a deflectable region having a tissue-engaging outer surface. The lead further includes a tendon disposed at least partially within the body and attached to the body under tension at a first attachment location distal to the deflectable region. Tension in the tendon maintains the deflectable region in a deflected shape in which the tissue-engaging outer surface can frictionally engage an inner wall of the cardiac vessel.

The present invention, in another embodiment, is a medical electrical lead comprising an elongate body defining a proximal region and a distal region. The distal region is configured to be partially implanted in a cardiac vessel and includes at least one electrode on the body, and first and second deflectable regions. The lead further includes a first tendon housed at least partially within and attached to the lead body under tension at a first attachment location distal to the first deflectable region, and a second tendon housed at least partially within and attached to the lead body under tension at a second attachment location distal to the second deflectable region. Tension in the first and second tendons maintains the first and second deflectable regions in deflected states.

The present invention, in yet another embodiment, is a method for fixation of a cardiac lead in a cardiac vessel, the lead including an elongate body defining a proximal region and a distal region, a conductor within the body, a deflectable region, and a tendon disposed within and operatively connected to the body at an attachment location distal to the deflectable region. The method comprises first transvenously delivering the lead such that the deflectable region is located within the cardiac vessel in an undeployed configuration. The method further includes applying a tensile force to the tendon to proximally displace the tendon relative to the proximal region. The tensile force is transmitted through the tendon to the lead body at the attachment location so as to deflect the deflectable region and cause a tissue engaging surface of the deflectable region to engage a wall of the cardiac vessel.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
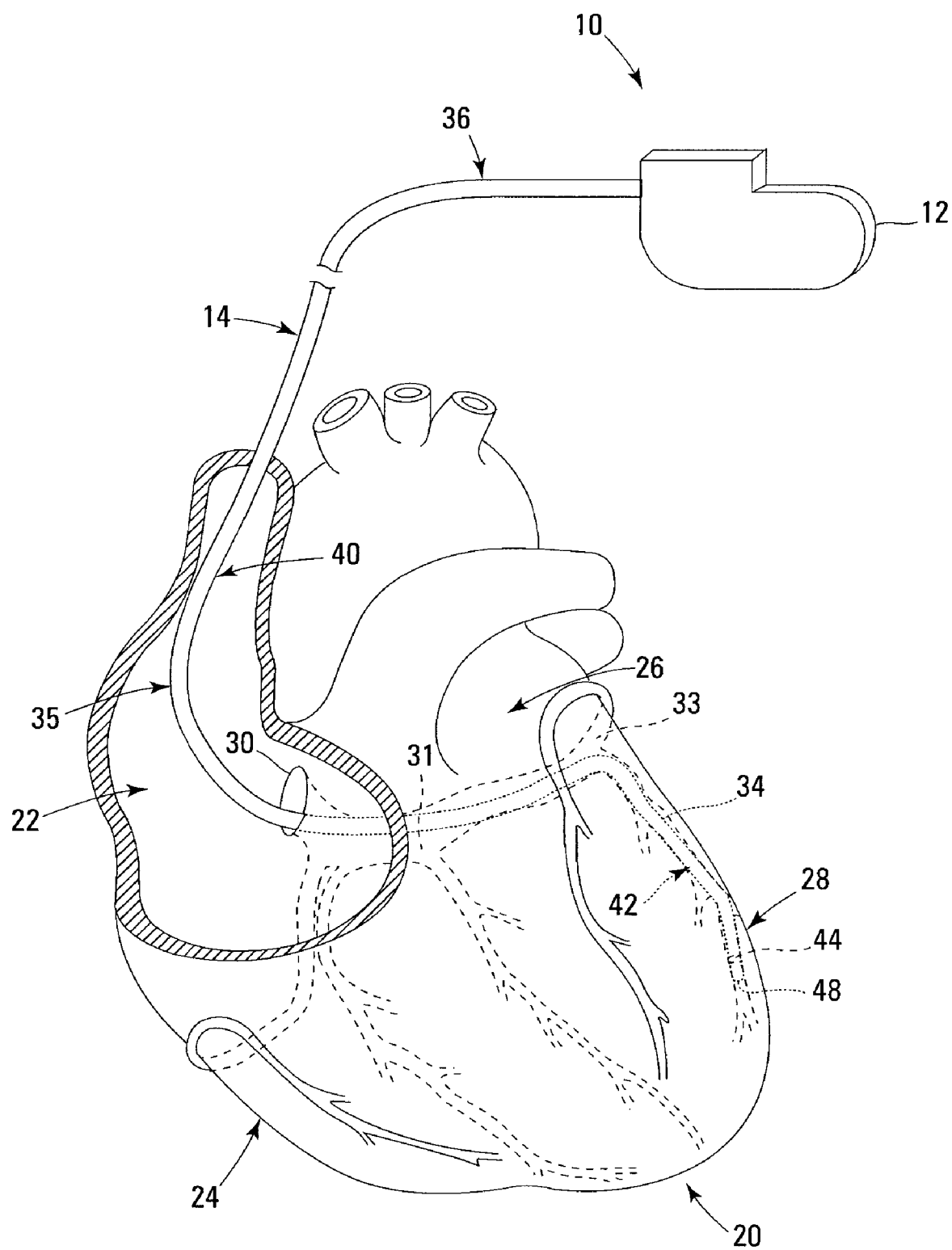
FIG. 1 is a schematic drawing of a cardiac rhythm management system including a pulse generator coupled to a lead deployed in a patient's heart according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic drawing of a cardiac rhythm management system 10 including a pulse generator 12 coupled to a lead 14 deployed in a patient's heart 20, which includes a right atrium 22 and a right ventricle 24, a left atrium 26 and a left ventricle 28, a coronary sinus ostium 30 in the right atrium 22, a coronary sinus 31, and various coronary veins including a great cardiac vein 33 and other branch vessels off the coronary sinus 31 including an exemplary branch vessel 34.

As shown in FIG. 1, the lead 14 includes an elongate body 35 defining a proximal region 36 and a distal region 40. The distal region 40 has a distal end portion 42 including at least one electrode 44 and terminating in a distal tip 48. In the embodiment illustrated in FIG. 1, the distal region 40 is guided through the right atrium 22, the coronary sinus ostium 30, and the coronary sinus 31, and into the branch vessel 34 of the coronary sinus 31, with the distal end 42, and thus the electrode 44 and the distal tip 48, positioned within the branch vessel 34. The illustrated position of the lead 14 may be used, for example, for sensing physiologic parameters and delivering a pacing and/or defibrillation stimulus to the left side of the heart 20. Additionally, it will be appreciated that the lead 14 may also be partially deployed in other cardiac vessels such as the great cardiac vein 33 or other branch vessels for providing therapy to the left side of the heart 20.

The lead 14, and other such leads according to the present invention, exemplary embodiments of which are shown and discussed in detail below, includes one or more fixation features adapted to frictionally engage an interior surface of one or more of the cardiac vessels (e.g., the coronary sinus 31 and the branch vessel 34) to prevent, or substantially impede displacement and dislodgement of the distal end portion 42, and in particular, the electrode 44, from the branch vessel 34 (or other target cardiac vessel). In some embodiments, these fixation features advantageously provide acute fixation without interfering with delivery of the lead to the desired implantation position. Additionally, if desired, the fixation features can provide chronic fixation or, alternatively, can be adapted to permit repositioning and/or removal of the lead from the body when appropriate.

Figure 2A:
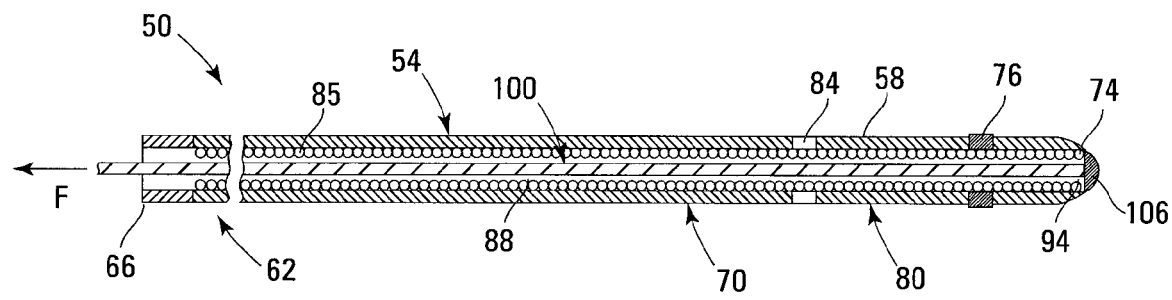
FIG. 2A is a cross-sectional view of a lead including an exemplary fixation feature according to one embodiment of the present invention.

FIG. 2A is a cross-sectional view of a lead 50 according to one embodiment of the present invention. As illustrated in FIG. 2A, the lead 50 has an elongate lead body 54 with an outer surface 58, the body 54 defining a proximal region 62 having a proximal end 66, and a distal region 70 terminating at a distal tip 74 and including at least one electrode 76. The distal region 70 includes a fixation feature, which in the illustrated embodiment includes a deflectable region 80 extending from a deflection location 84 to the distal tip 74. As shown, the lead 50 further includes an insulated conductor coil 85 within the lead body 54. In one embodiment, the lead body 54 provides an insulating sheath for the conductor 85. The conductor coil 85 forms an inner wall defining a lumen 88 extending from the proximal end 66 through a distal opening 94 in the distal tip 74. A tendon 100 is housed within body 54, and extends from proximally beyond the proximal end 66 to an attachment structure 106 located at the distal tip 74. In the illustrated embodiment, the tendon 100 is disposed within the lumen 88.

In the illustrated embodiment, the attachment structure 106 is located outside the distal opening 94, and operates to prevent the tendon 100 from retracting proximally within the lumen 88. In other embodiments, the tendon 100 is attached to the lead 50 via an alternative attachment structure and at an attachment location proximal to the distal tip 74. That is, the tendon 100 can be attached to the lead 50 at any location providing the desired operability, as discussed below. In some embodiments, the tendon 100 may be disposed within a secondary lumen rather than the lumen 88 formed by the conductor coil 85 as illustrated in FIG. 2A.

The deflectable region 80 provides a deployable fixation feature adapted to change between an undeflected (i.e., undeployed) configuration as shown in FIG. 2A, and a deflected (i.e., deployed) configuration. In its deployed configuration, the lead outer surface 58 provides a tissue engaging surface adapted to frictionally engage the inner surface of one of the cardiac vessels (e.g., the coronary sinus 31 and the branch vessel 34) in which the lead 14 is positioned. The tendon 100 operates to transmit a proximally directed tensile force to the lead 50 at the attachment location (i.e., in the illustrated embodiment, the distal tip 74), thereby causing a shape change in the deflectable region 80. The deflection location 84 provides a point or localized region at which the deflectable region 80 can preferentially deflect. In the illustrated embodiment, the attachment structure 106 prevents the tendon 100 from retracting proximally through the lumen 88 when such a force is applied. As discussed above, the form of attachment structure 106 shown in FIG. 2A is exemplary only, and in other embodiments, the tendon 100 may be fixedly attached directly to the inner wall of the lumen 88. In short, any structure for attaching the tendon 100 to the lead 14 may be used.

Figure 2B:
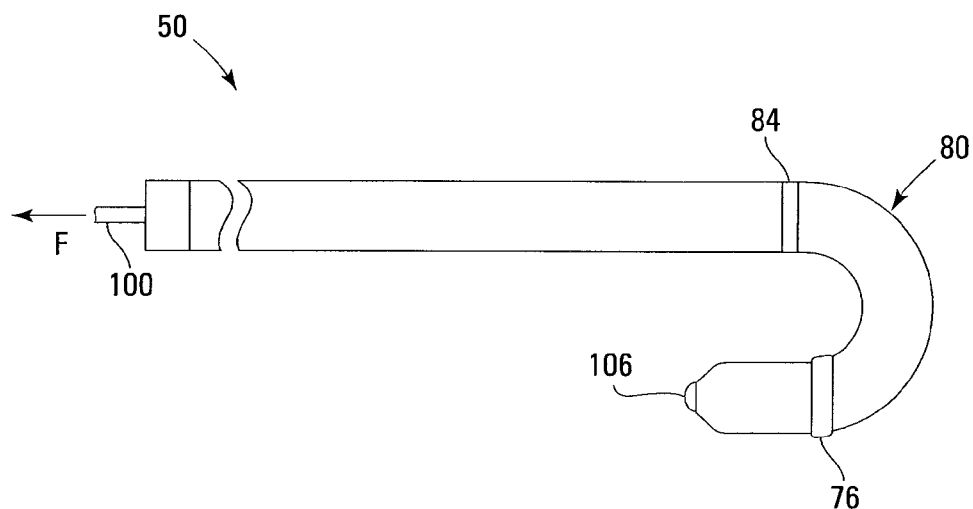
FIG. 2B depicts the lead of FIG. 2A with the fixation feature in undeployed and deployed configurations.

FIG. 2B illustrates the lead 14 showing the deflectable region 80 in the deflected (i.e., deployed) configuration. As shown in FIG. 2B, because the tendon 100 is fixedly attached to the lead 50 at the distal tip 74, applying a tensile force F to the tendon 100 while restraining the proximal region 62 from being proximally displaced (i.e., by grasping and holding the proximal region 62 in place while applying the tensile force) causes the tendon 100 to move proximally relative to the proximal region 62. This in turn causes the deflectable region 80 to deflect at the deflection location 84. Such deflection causes the lead body outer surface 58 to contact and frictionally engage the inner wall of the cardiac vessel (e.g., the coronary sinus 31 or branch vessel 34) in which the deflectable region 80 is positioned. The tendon 100 may then be secured under tension to the lead body 54 at a proximal attachment location at or near the proximal end 66 to maintain the deflectable region 80 in the deployed configuration for fixation.

In the illustrated embodiment, the deflectable region 80 is configured to attain a deflected shape in the form of a "J" when deployed. The shape of the deflectable region 80 in the deployed configuration can be controlled by various factors including, for example, the configuration, number, and spacing of deflection locations 84, attachment location of the tendon 100 to the lead 50, the inherent stiffness of the deflectable region 80, and the magnitude of the proximally directed force F applied to the tendon 100 (i.e., the amount of proximal displacement of the tendon 100 relative to the lead body 54). Thus, varying these parameters can provide a wide range of deployed deflectable region shapes.

The operability of the deflectable region 80 can also be affected by varying the attachment location of the tendon 100 to the lead 50. As discussed above, the tendon 100 can be attached to the lead 50 at any attachment location along the lead 50. For example, in one embodiment, the tendon 100 is attached to the lead 50 at a location proximal to the distal tip 74 such that the distal most portions of the deflectable region 80 remain relatively flexible. This can be desirable, for example, because it permits the distal most portion of the lead 50 to flex with the natural motion of the heart.

Figure 2C:
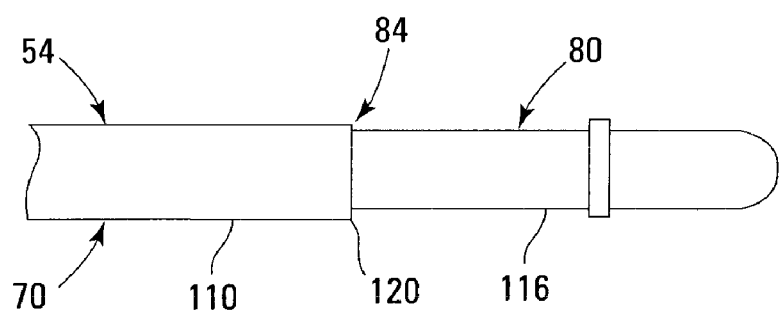
FIGS. 2C-2F are partial cross-sectional views of the distal region of the lead of FIGS. 2A-2B including various embodiments of the fixation feature.

FIGS. 2C-2F depict portions of the distal region 70 including the deflectable region 80 of the lead and illustrating exemplary deflection location 84 configurations according to various embodiments of the present invention. As shown in FIG. 2C, the lead body 54 includes a relatively stiff portion 110 and a relatively flexible portion 116 located distal to the stiff portion 110. In this embodiment, the deflection location 84 is created in the lead body 54 by a transition 120 between the relatively stiff and relatively flexible portions 110, 116. The relatively flexible portion 116 is pliable and will preferentially bend with respect to the stiff portion 110 under a given proximal force F to the tendon 100. In one embodiment, the stiff portion 110 is formed by using a relatively rigid material, e.g., polyurethane, in the lead body 54, and the flexible portion 116 is formed from a more pliable material, e.g., silicone. In another embodiment, the stiff portion 110 may have a greater wall thickness than the flexible portion 116. In another embodiment, the relatively stiff portion 110 may be reinforced (e.g., by a metal or fabric braid material embedded beneath the outer surface 58) to increase its stiffness, while the relatively flexible portion 116 may be unreinforced. Alternatively, both portions 110, 116 may be reinforced with the relatively stiff portion 110 being more extensively reinforced than the relatively stiff portion 116.

Figure 2D:
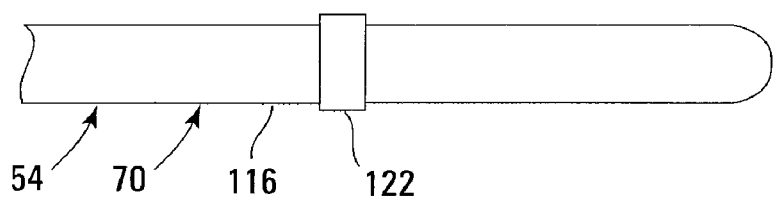

In FIG. 2D, the deflection location 84 is formed by an electrode 122 on the lead body 54, which locally stiffens the lead body 54 and causes the more flexible portion distal the electrode 122 to preferentially deflect upon the application of the tensile load to the tendon 100.

Figure 2E:
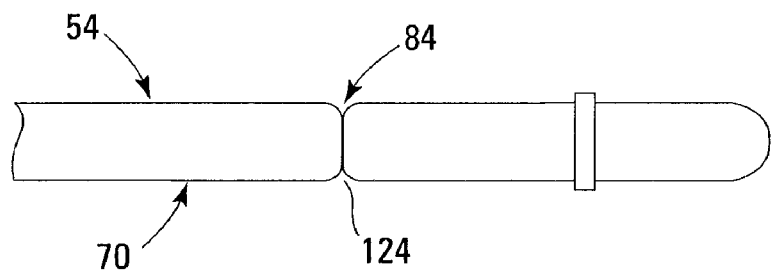
Figure 2F:
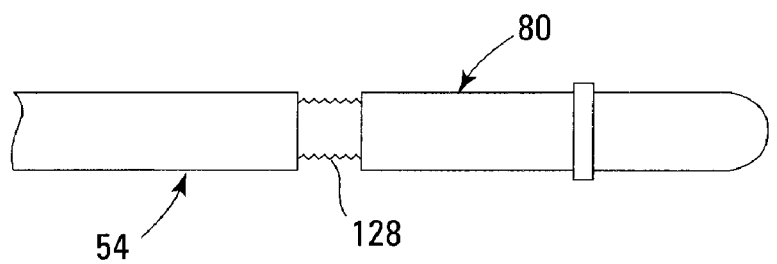

In FIG. 2E the deflection location 84 includes a notch 124 in the lead body 54, which creates a localized point about which the deflectable region 80 can deflect. FIG. 2F illustrates a similar approach in which a cutout 128 is made in the lead body 54, in which a section of the insulating sheath of the lead body 54 is removed to create the deflection location 84.

The embodiments illustrated in FIGS. 2C-2F for creating the deflection location 84 may, in some embodiments, be combined to further vary the shape of the deflectable region 80 when in the deployed configuration. For example, a lead 50 may include a deflection location 84 including the transition 120 between the stiff and flexible portions 110, 116, as well as the notch 124. Additionally, in some embodiments, the deflectable region 80 of the lead 50 may include more than one deflection location 84 to vary the deflected shape of the deflectable region 80. Moreover, the illustrated deflection location embodiments are in no way limiting. To the contrary, any configuration or feature which creates a point or zone about which the deflectable region 56 can deflect can be used.

Figure 3A:
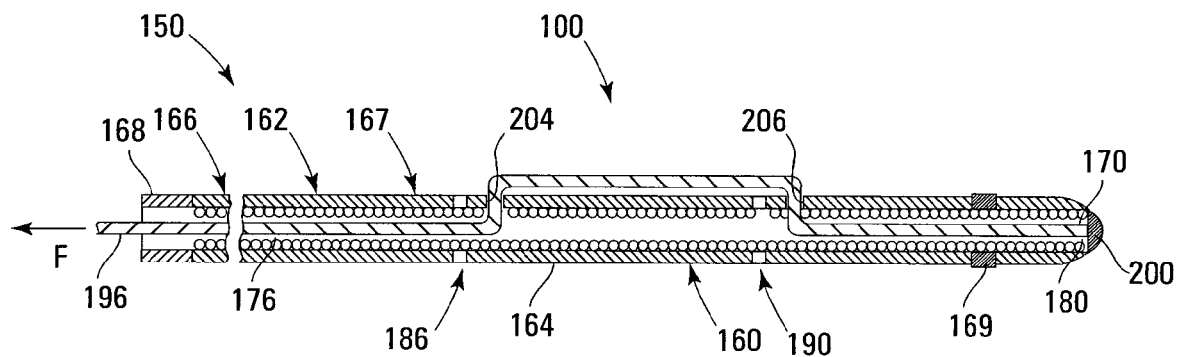
FIG. 3A is a partial cross-sectional view of a lead including a deflectable fixation feature according to another embodiment of the present invention.

FIG. 3A is a partial cross-sectional view of a lead 150 showing a deflectable region 160 according to another embodiment of the present invention. As shown in FIG. 3A, the lead 150 includes a body 162 having an outer surface 164 and defining a proximal region 166 and a distal region 167. The proximal region 166 includes a proximal end 168, and the distal region includes an electrode 169 and terminates in a distal tip 170. A lumen 176 extends from to the distal tip 170 and terminates in an open distal end 180. The deflectable region 160 includes first and second deflection locations 186, 190. A tendon 196 is housed within the body 162, and extends from the proximal end 168 to the distal tip 170 and includes an attachment structure 200 adapted to fixedly attach the tendon 196 to the lead body 162. In the illustrated embodiment, the tendon 196 is disposed within the lumen 176, and extends through the body 162 at apertures 204 and 206, thus defining a portion of the tendon 196 extending along the outer surface 164 of the lead body 162.

As with the lead 50 described above, the deflectable region 160 provides a fixation feature adapted to change between an undeflected (i.e., undeployed) shape as shown in FIG. 3A, and a deflected (i.e., deployed) shape in which the lead outer surface 164 provides a tissue engaging surface adapted to frictionally engage the inner surface of one of the cardiac vessels (e.g., the coronary sinus 31 and the branch vessel 34) through which the lead 150 is delivered. The tendon 196 operates to transmit a proximally directed force applied to the tendon 196 to the distal tip 170, thereby changing the shape of (i.e., deploying) the deflectable region 160. The deflection locations 186, 190 are adapted to control the points of deflection of the deflectable region 160. The deflection locations 186, 190 may be configured according to any of the embodiments described above with respect to the lead 50. It will further be appreciated that any other configuration for providing points at which the deflectable region can deflect may be used within the scope of the present invention.

Figure 3B:
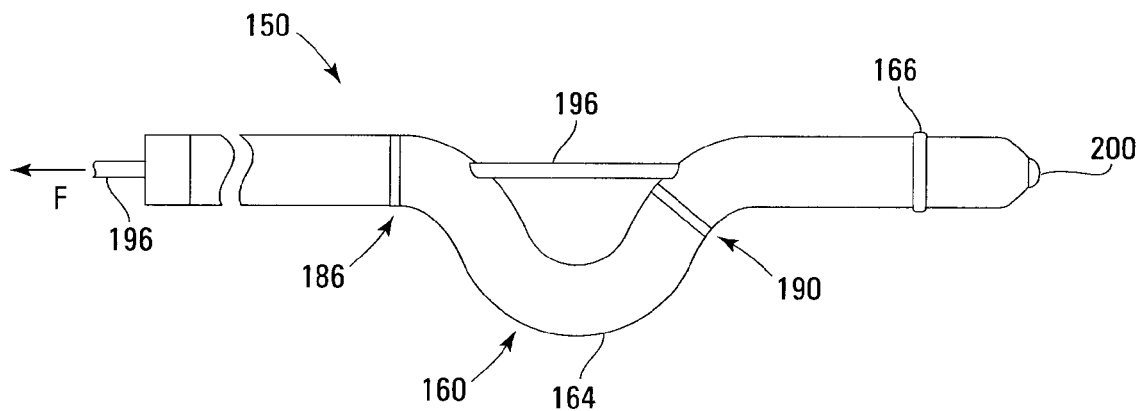
FIG. 3B illustrates the lead of FIG. 3A with the deflectable fixation feature in the deflected (i.e., deployed) configuration.

FIG. 3B illustrates the lead 150 with the deflectable region 160 in the deflected (i.e., deployed) configuration. As shown in FIG. 3B, applying a tensile force F to the tendon 196 while restraining the proximal region 166 from being proximally displaced (i.e., by grasping and holding the proximal region 166 in place while applying the tensile force) causes the tendon 196 to move proximally relative to the proximal region 166. This in turn causes the deflectable region 160 to deflect at the deflection locations 186, 190, thus changing the shape of the deflectable region 160 as illustrated in FIG. 3B. Such deflection causes the lead body outer surface 164 to contact and frictionally engage the inner wall of the cardiac vessel (e.g., the coronary sinus 31 or branch vessel 34) in which the deflectable region 80 is positioned. The tendon 196 may then be secured under tension to the lead body 162 at or near the proximal end (not shown). In the illustrated embodiment, the portion of the lead 150 distal to the deflection location 190 is relatively stiff, such that it remains substantially undeflected under the action of the tensile force F on the tendon 196. Alternatively, in other embodiments, all or part of the portion of the lead 150 distal to the deflection location 190 can be made relatively flexible so as to undergo some deflection under the action of this tensile force F.

Although the illustrated deflectable region 160 includes two deflection locations 186, 190, other embodiments may include more than two deflection locations to create additional fixation feature shapes. For example, in one embodiment, three or more deflection locations are employed to provide a sinusoidal deflected shape to the lead when in the deployed configuration. Additionally, the deflection locations 84 and 186, 190 of the leads 50 and 150, respectively, may, in some embodiments, be strategically positioned on the lead bodies so as to control the direction of deflection of the respective deflectable regions. For example, in some embodiments, a plurality of deflection locations can be provided, each extending only partially around the circumference of the lead, and at least some being offset from one another about the circumference of the lead body. In such an embodiment, each such deflection location will tend to cause the lead body to deflect in a different direction, creating a deployed configuration having a three-dimensional shape. It will thus be appreciated that selectively positioning and configuring the deflection location(s) and the deflectable region(s) can produce a wide range of shapes for fixation.

In addition, in still other embodiments, the leads 50 and/or 150 can include more than one tendon, each attached to the respective lead body at a different attachment location. In one embodiment, the lead may include a first tendon attached to the lead body at a first attachment location at or near the distal tip, and a second tendon attached to the lead body at a location proximal to the distal tip. For example, the lead 50 and/or 150 may be configured to have a compound shape in the deployed configuration which is a combination of the J- and S-shaped configurations of FIGS. 2B and 3B. Thus, a range of shapes can be achieved, particularly when multiple tendons are used in combination with strategically configured deflection locations. Alternatively, the lead 50 and/or 150 can include multiple tendons, each operable to deflect a different deflectable region of the lead. In such embodiments, the physician can select the optimal deployed configurations based on the particular patient's vascular anatomy. In multi-tendon embodiments, one or more of the plurality of tendons can be disposed within one or more secondary lumens and not within the lumen formed by the main conductor coil as illustrated in FIG. 3A.

Figure 3C:
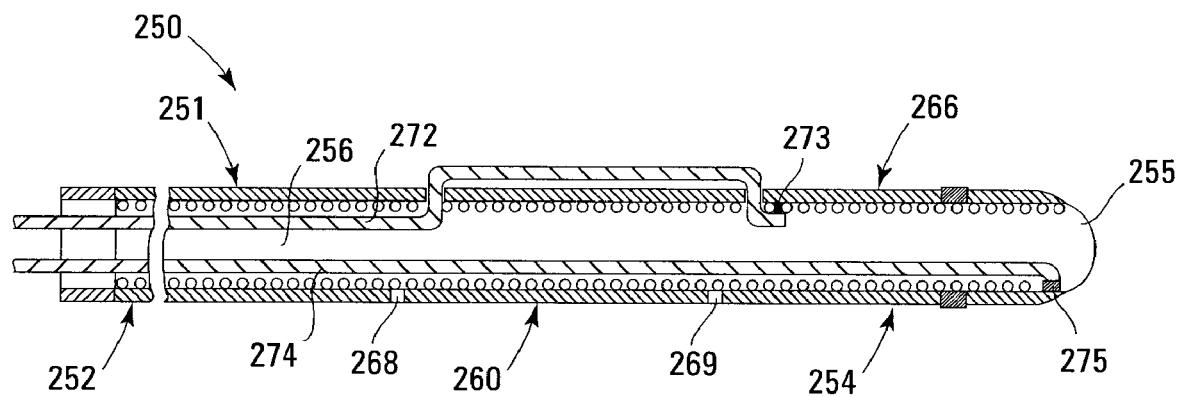
FIG. 3C illustrates a lead including a plurality of deflectable fixation features according to another embodiment of the present invention.

FIG. 3C illustrates an exemplary multi-tendon lead 250. As shown in FIG. 3C, the lead 250 is in many respects similar or identical to the leads 50 and 150 described above, and includes a body 251 defining a proximal portion 252, a distal portion 254 terminating in a distal tip 255, and a lumen 256 throughout. The distal portion 254 includes first and second deflectable regions 260, 266. A first deflection location 268 is located on the body 251 proximal to the first deflectable region 260, and a second deflection location 269 is located on the body 251 between the first and second deflectable regions 260, 266. As further shown, the lead 250 includes a first tendon 272 housed partially within the body 251 in the lumen 256 and attached to the body 251 at a first attachment location 273 distal to the second deflection location 269. The lead 250 further includes a second tendon 272 housed partially within the body 251 in the lumen 256 and attached to the body 251 at a second attachment location 275 proximate the distal tip 255.

In the embodiment illustrated in FIG. 3C, the first tendon 272 is operable to cause deployment of the first deflectable region 260 in the manner described above. Additionally, the second tendon 274 can be operable to cause deflection of the second deflectable region 266 and/or the first deflectable region 260. For example, the lead 250 can be configured (e.g., by differentiating the relative stiffness of the first and second deflectable regions 260, 266) such that upon the application of a tensile force to the second tendon 274, the second deflectable region 266 will preferentially deflect at the second deflection location 268. The lead 250 can further be configured such that the first deflectable region 260 can be subsequently deflected by increasing the tensile force on the second tendon 274.

The deflectable fixation features of the leads 50, 150, and 250 described above also advantageously allow the physician to return the leads to their undeployed configurations (i.e., by relieving the tensile load on the respective tendons) for repositioning and/or removing the lead as desired. In addition, if desired, the deflectable regions described above permit the physician to selectively urge the lead electrode(s) into intimate contact with the target vessel wall. The deflectable regions of the leads 50, 150, 250 also can facilitate delivery of the leads by effectively permitting the physician to steer the leads through the tortuous coronary vasculature to the desired implantation site.

In some embodiments, the tissue-engaging outer surfaces of the leads 50, 150, 250, particularly in their respective deflectable regions, may include features to enhance engagement with the inner surface of the target coronary vessel. Such features may include, for example, surface roughening, adhesive or sticky coatings, and fibrosis-promoting coatings. Alternatively, to facilitate extraction of the lead after long-term implantation, the deflectable regions may include coatings (e.g., polymer coatings such as PTFE) or other features to discourage tissue ingrowth.

Figure 4A:
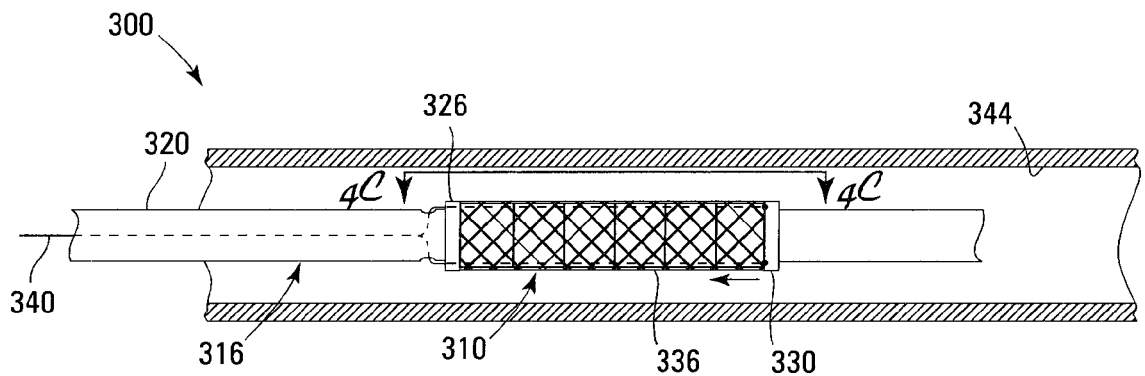
FIGS. 4A and 4B illustrate a distal region of a lead within a body lumen (which as illustrated is a branch vessel of the coronary sinus) including an expandable fixation mechanism according to another embodiment of the present invention.
Figure 4B:
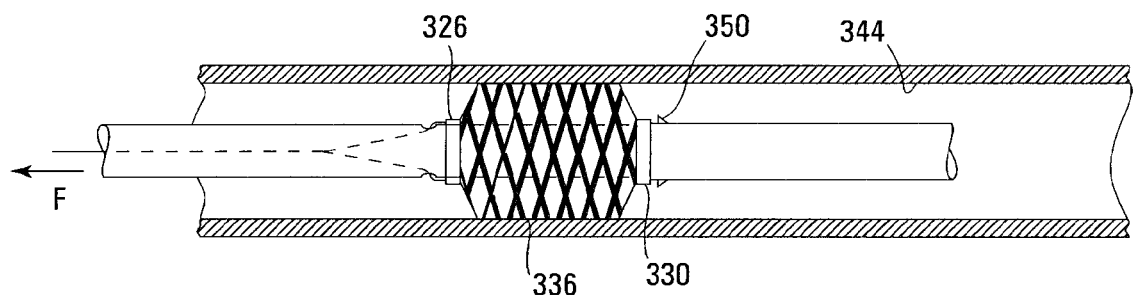

FIGS. 4A and 4B illustrate a portion of a distal region of a lead 300 within a body lumen (which as illustrated is the branch vessel 34) including an alternative fixation feature, which as illustrated is an expandable fixation mechanism 310 according to another embodiment of the present invention. As shown in FIG. 4A, the lead 300 includes a lead body 316 having an outer surface 320. The fixation mechanism 310 is disposed on the lead body 316 and includes a proximal anchor 326, a distal floating ring 330, and a radially expandable structure 336 attached at opposite ends to the anchor 326 and the ring 330. A tendon 340 is disposed within the body (e.g., within a lumen, not shown) and attached to one or more locations on the ring 330. The position of the anchor 326 on the body 316 is fixed, while the distal ring 330 is a floating member adapted to translate along the body 316. In the illustrated embodiment, the anchor 326 is a ring fixedly attached to the lead body 316. In other embodiments, the anchor 326 may have structures other than a ring. In one embodiment, the radially expandable structure 336 is fixedly attached at one end directly to the lead body 316 to form the anchor 326.

The radially expandable structure 336 can expand from a radially collapsed (i.e., undeployed) configuration as shown in FIG. 4A, to a radially expanded (i.e., deployed) configuration as shown in FIG. 4B in which the radially expandable structure 336 extends radially beyond the outer surface 320 of the lead body 316. In the radially expanded configuration, the radially expandable structure 336 is adapted to fix the lead 300 in a desired implantation location by frictionally engaging an inner surface 344 of the branch vessel 34. In the illustrated embodiment, the radially expandable structure 336 is a stent-like device resembling stents known in the art for use in vascular intervention procedures. In other embodiments, the radially expandable structure 336 may have other configurations such as, for example, a radially expandable coil or a plurality of randomly oriented wires connected between the anchor 326 and the ring 330.

In one embodiment, the radially expandable structure 336 is normally in the radially collapsed configuration as shown in FIG. 4A for delivery of the lead 300, and a proximally directed tensile force is applied to the tendon 340 to pull the tendon 340, and in turn, the ring 330, proximally relative to the lead body 316, thereby causing the radially expandable structure 336 to expand radially to the configuration shown in FIG. 4B. In one such embodiment, the tendon 340 may be maintained under tension to retain the radially expandable structure 336, and thus the fixation mechanism 310, in the deployed, radially expanded configuration. In such embodiments, the tendon 340 may be secured to the lead body 316 after deploying the fixation mechanism 310. The fixation mechanism 310 can further be returned to the radially collapsed configuration of FIG. 4A by releasing the tension in the tendon 340, thus permitting removal and/or repositioning of the lead 300.

Alternatively, in one embodiment, the lead 300 may include a retention structure such as one or more deflectable stops 350 on the body 316 which may be deflected downward to permit proximal movement of the ring 330 for deployment of the fixation mechanism 310, but which, once engaged, prevent subsequent distal movement of the ring 330. It is emphasized, however, that any other structures or methods for retaining the fixation mechanism 310 in the deployed configuration of FIG. 4B may be used.

In another embodiment, the radially expandable structure 336 is self-expanding and is retained in the radially collapsed configuration of FIG. 4A by, for example, a retention structure (not shown) preventing spontaneous proximal movement of the ring 330 but which can be disengaged or overcome by a sufficient proximally directed force applied to the tendon 340. Once the retention structure is thus disengaged, the radially expandable structure 336 can self-expand to the configuration of FIG. 4B. Both of the latter two embodiments advantageously allow the tension in the tendon 340 to be removed after deployment of the fixation structure 310. Additionally, in such embodiments, the tendon 340 may be detachable from the fixation mechanism 310, thus permitting removal of the tendon 340 from the lead 310 after implantation.

Figure 4C:
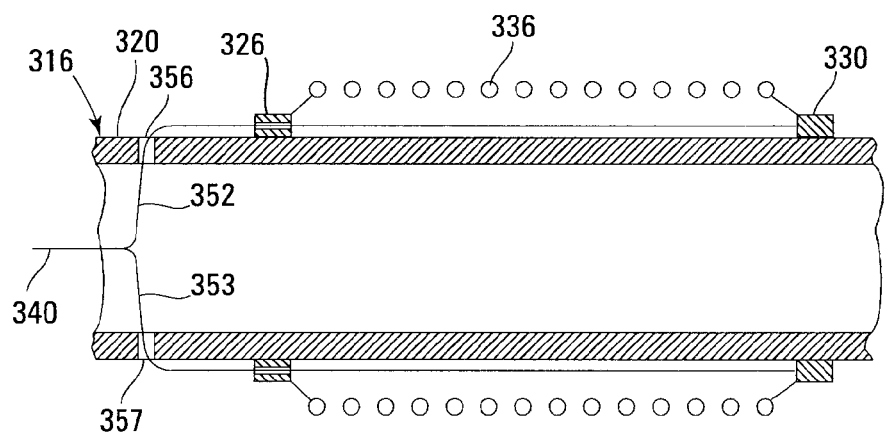
FIG. 4C is a partial cross-sectional view of the lead of FIGS. 4A-4B showing one exemplary structure for attaching a tendon to the fixation mechanism.

FIG. 4C is a partial cross-sectional view of the lead 300 and the fixation mechanism 310 showing one exemplary structure for attaching the tendon 340 to the ring 330. As shown in FIG. 4C, the tendon 340 includes diverging segments 352 and 353 extending through apertures 356 and 357, respectively, in the lead body 316. As further shown, the tendon segments 352, 353 extend along the lead body 316 between the radially expandable structure 336 and the outer surface 320 and are attached to the ring 330. In the illustrated embodiment, the apertures 356, 357 are located proximal to the anchor 326, although in other embodiments the apertures may be located between the anchor 326 and the ring 330. In some embodiments, more than two tendon segments may be used. As is apparent from FIG. 4C, as the tendon 340 is pulled proximally relative to the lead body 316 to deploy the fixation mechanism 310, the tendon segments 352, 353 retract through the apertures 356, 357 and into the lead lumen. It is emphasized, however, that the tendon attachment embodiment illustrated in FIG. 4C is exemplary only, and that any structures or methods for operatively coupling the tendon 340 to the ring 330 may be used within the scope of the invention.

In another embodiment, the fixation mechanism 310 may be configured such that it does not extend radially beyond the outer surface 320 of the lead body 316 when in the undeployed, radially collapsed configuration. For example, the lead 300 may, in such an embodiment, include a reduced-diameter portion of the lead body 316, and the fixation mechanism 310 may reside in this reduced-diameter portion. This configuration may promote ease of delivery of the lead 300 due to the lack of fixation structures protruding beyond the lead body during such delivery.

Figure 5A:
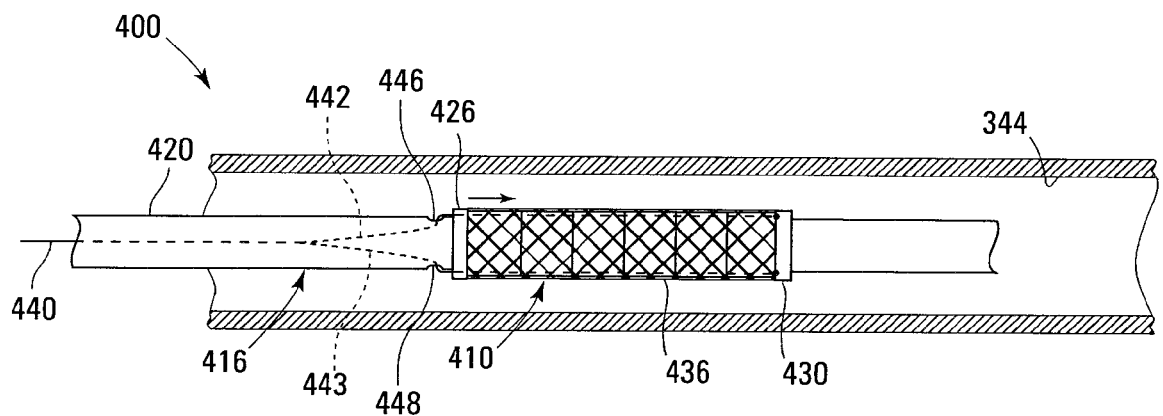
FIGS. 5A and 5B illustrate a distal region of a lead including a self-expanding fixation mechanism according to another embodiment of the present invention.
Figure 5B:
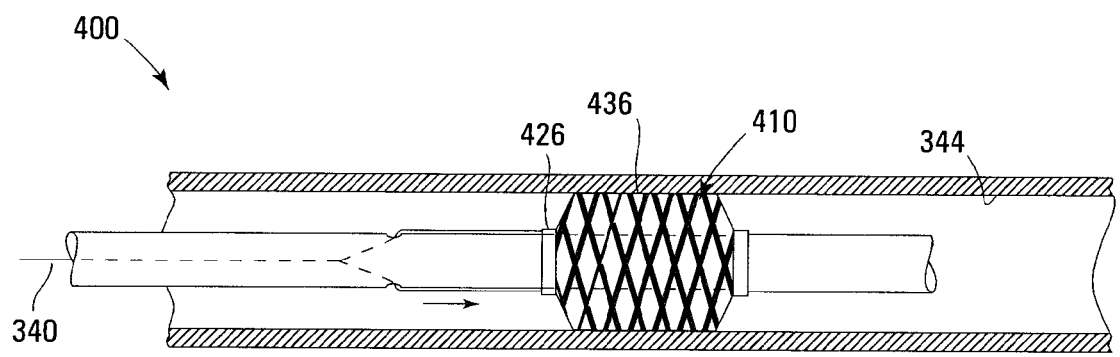

FIGS. 5A and 5B illustrate a portion of a distal region of a lead 400 including an alternative fixation feature, which as illustrated is a self-expanding fixation mechanism 410 according to another embodiment of the present invention. As shown in FIGS. 5A and 5B, the lead 400 includes a body 416 on which the fixation mechanism 410 is disposed. As further shown, the fixation mechanism 410 includes a proximal floating ring 426, a distal anchor 430, and a radially self-expanding structure 436 attached at opposite ends to the proximal ring 426 and the anchor 430. A tendon 440 is disposed within the lead body 416 (e.g., within a lumen, not shown) and attached to one or more locations on the ring 426. The position of the anchor 430 on the body 416 is fixed, while the ring 426 is a floating member adapted to translate along the body 416. In the illustrated embodiment, the anchor 426 is a ring fixedly attached to the lead body 416. In other embodiments, the anchor 426 may have structures other than a ring. In one embodiment, the radially expandable structure is fixedly attached at one end directly to the lead body 416 to form the anchor 426.

In the illustrated embodiment, the tendon 440 includes individual segments 442 and 443 extending through apertures 446, 448, respectively, in the lead body 416 and attached to the ring 426. In other embodiments, an alternative structure for attaching the tendon 440 to the ring 426 may be used. The self-expanding structure 436 is substantially similar in design and function to the self-expanding embodiment of the radially expandable structure 336 described above.

A tensile force applied to the tendon 440 operates to pull the ring 426 in the proximal direction to retain the self-expanding structure 436 in the radially collapsed configuration of FIG. 5A for delivery of the lead 400. In one embodiment, the lead 400 may be delivered to the desired implantation position with the tendon 440 secured, under tension, near the proximal end (not shown) of the lead 400. Once the lead 400 is delivered to the desired implantation location, the tension in the tendon 440 is released, and the self-expanding structure expands to the deployed configuration of FIG. 5B.

The embodiment of FIGS. 5A and 5B advantageously allows the tendon 340 to remain in the unloaded state (i.e., not under tension) after the lead is fixed by the fixation mechanism 410. Additionally, the fixation mechanism 410 can be returned to the radially collapsed state of FIG. 5A if desired, for example, to reposition and/or remove the lead 400 from the body.

The fixation mechanisms 310, 410 may be made from a variety of materials (e.g., metals, polymers) suitable for implantable devices. By way of example only, suitable materials include stainless steel and a wide variety of alloys and polymers. In some embodiments, the fixation mechanisms 310, 410 are made at least partially from materials having desirable shape memory and superelastic properties. For the self-expanding fixation mechanisms, one exemplary material exhibiting suitable shape memory and superelasticity is Nitinol. Other suitable materials will be ascertained by those skilled in the art based on the foregoing.

It will be appreciated that in some embodiments, the fixation mechanism 410 may be configured such that it does not extend radially beyond the outer surface 420 of the lead body 416 when in the radially collapsed configuration. For example, the lead 400 may, in such an embodiment, include a reduced-diameter portion of the lead body 416, and the fixation mechanism 410 may reside in this reduced-diameter portion. This configuration may promote ease of delivery of the lead 400.

Figure 6A:
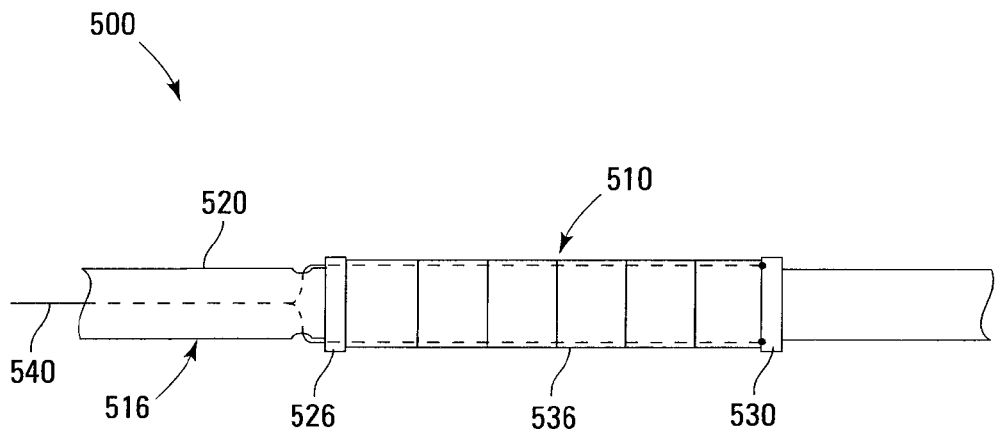
FIGS. 6A and 6B illustrate a distal region of a lead including an expandable fixation mechanism according to one embodiment of the present invention.
Figure 6B:
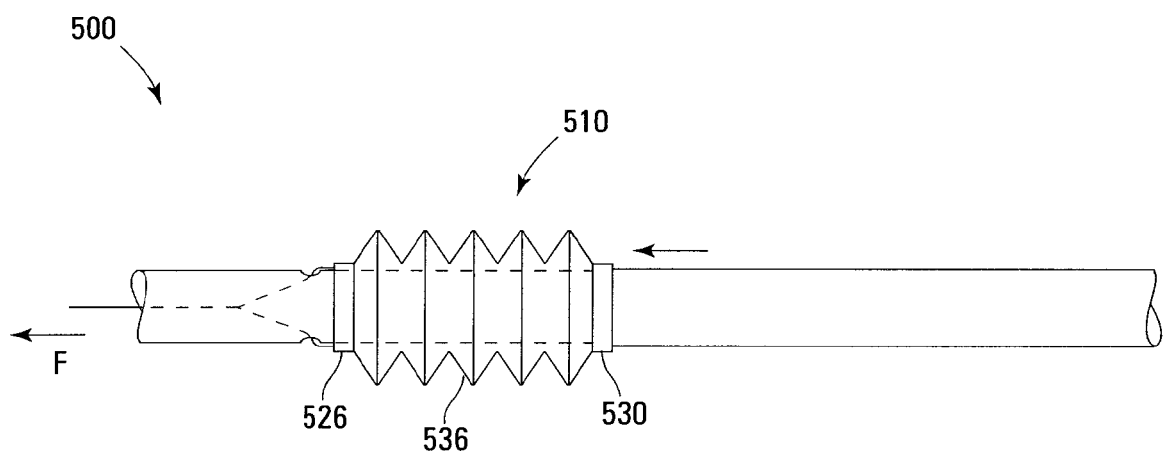

FIGS. 6A and 6B illustrate a portion of a distal region of a lead 500 including an alternative fixation feature, which as illustrated is a radially expandable fixation mechanism 510 according to another embodiment of the present invention. As shown in FIG. 6A, the lead 500 includes a lead body 516 having an outer surface 520. The fixation mechanism 510 is disposed on the lead body 516 and includes a proximal anchor 526, which in the illustrated embodiment is in the form of a ring attached to the body 516, a distal floating ring 530, and a radially expandable structure which in the illustrated embodiment is a bellows 536 attached at opposite ends to the anchor 526 and the ring 530. A tendon 540 is disposed within the lead body (e.g., within a lumen, not shown) and attached to one or more locations on the ring 530. In the illustrated embodiment, the tendon 540 is configured and attached to the ring 530 in the manner illustrated in FIG. 4C above. In other embodiments, an alternative structure for operatively attaching the tendon 540 to the ring 530 may be used. The position of the anchor 526 on the body 516 is fixed, while the ring 530 is a floating member adapted to translate along the body 516.

The fixation mechanism 510 operates in a manner substantially similar to the fixation mechanism 310 described above. Thus, in one embodiment, the radially expandable bellows 536 are normally in the radially collapsed configuration as shown in FIG. 6A for delivery of the lead 500. Once the lead 500 is positioned in the body as desired, a proximally directed tensile force is applied to the tendon 540 to pull the tendon 540, and accordingly, the ring 530, proximally relative to the body 526, thereby longitudinally compressing the bellows 536, which radially expand to the deployed configuration shown in FIG. 6B. When so expanded, the bellows 536 can engage an inner surface of the cardiac vessel in which the fixation mechanism 510 is positioned, thus fixing the lead 500 in the implanted position.

In one embodiment, once the fixation mechanism 510 is deployed, the tendon 540 may be maintained under tension and secured to the lead body 516 to retain the bellows 536, and thus the fixation mechanism 510, in the deployed configuration. The fixation mechanism 510 can further be returned to the radially collapsed configuration of FIG. 6A by releasing the tension in the tendon 540, thus permitting removal and/or repositioning of the lead 500. Alternatively, the lead 500 may, in other embodiments, include one or more retention structures, such as the deflectable stops 350 of the lead 300 described above, for preventing movement of the ring 530 in the distal direction once the fixation mechanism 510 is deployed. In other embodiments (not shown), other or additional structures are provided for retaining the fixation mechanism 510 in the deployed configuration of FIG. 6B.

In other embodiments (not shown), the bellows 536 may be configured to be self-expanding, with the fixation mechanism 510 constrained in the radially collapsed configuration for delivery in much the same manner as the self-expanding embodiments of the fixation mechanisms 310 and 410 described above.

The bellows 536 may be made from any materials having the desired flexibility and biocompatibility properties. Exemplary materials include polymers such as polyurethane and polyetheretherketone (PEEK™), and metals such as stainless steel and Nitinol.

In some embodiments (not shown), the bellows 536 may include features (e.g., perforations or other cutouts) to reduce any potential occlusive effect and/or to encourage tissue ingrowth for chronic fixation. For example, in one embodiment, the bellows 536 extends only partially around the circumference of the lead 500. In one embodiment, the bellows 536 are in the form of a plurality of elongated lobes disposed radially around the lead body 516.

It will be appreciated that in some embodiments, the fixation mechanism 510 may be configured such that it does not extend radially beyond the outer surface 520 of the lead body 516 when in the radially collapsed configuration. For example, the lead 500 may, in such an embodiment, include a reduced-diameter portion of the lead body 516, and the fixation mechanism 510 may reside in this reduced-diameter portion. This configuration may promote ease of delivery of the lead 500.

Figure 7A:
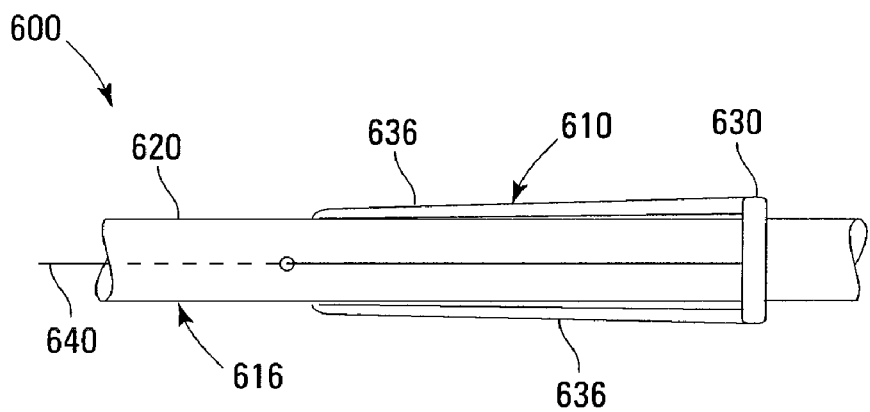
FIGS. 7A-7C illustrate a distal region of a lead including an expandable fixation mechanism according to another embodiment of the present invention.
Figure 7B:
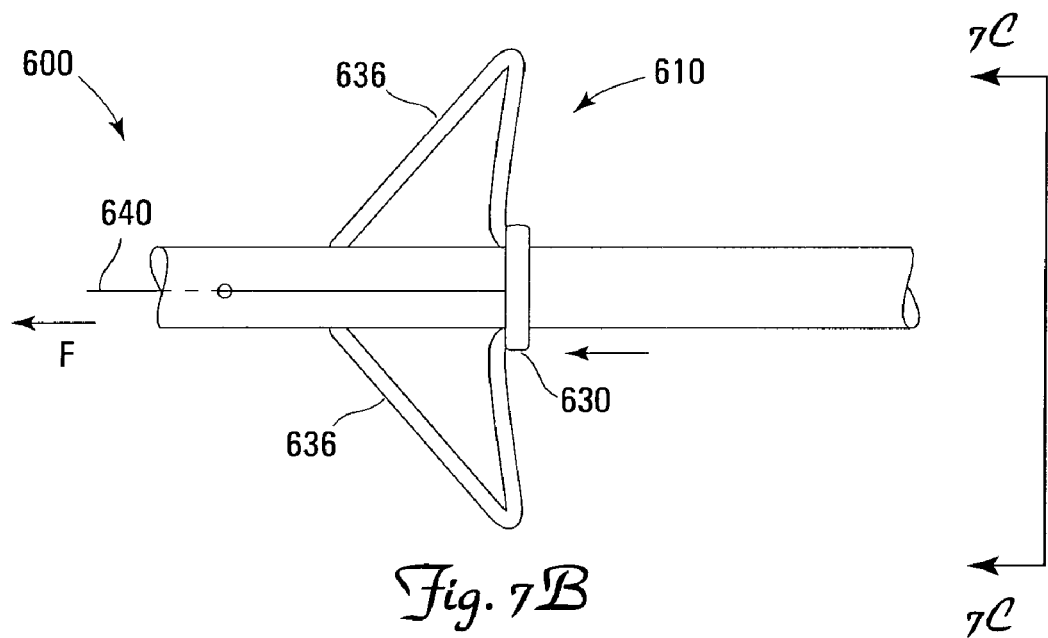

FIGS. 7A and 7B illustrate a portion of a distal region of a lead 600 including an alternative fixation feature, which as illustrated is a radially expandable fixation mechanism 610 according to another embodiment of the present invention. As shown in FIGS. 7A and 7B, the lead 600 includes a lead body 616 having an outer surface 620. The fixation mechanism 610 is disposed on the lead body 616 and includes a distal floating ring 630, and a plurality of radially expandable ribs 636 attached at opposite ends to the ring 630 and to the body 616. A tendon 640 is disposed partially within the body 616 (e.g., within a lumen, not shown) and attached to one or more locations on the ring 630. In the illustrated embodiment, the tendon 640 is configured and attached to the ring 630 in substantially the manner illustrated in FIG. 4C above. Other embodiments (not shown) may employ alternative structures and arrangements for attaching the tendon 640 to the ring 630. The ring 630 is a floating member adapted to translate along the lead body 616.

In one embodiment, the ribs 636 are normally in the radially collapsed configuration as shown in FIG. 7A for delivery of the lead 600. Once the lead 600 is positioned in the body as desired, a proximally directed tensile force is applied to the tendon 640 to pull the tendon 640 and the ring 630 proximally relative to the lead body 616, thereby causing the central portions of the ribs 636 to expand radially to the configuration shown in FIG. 7B for engaging the inner surface of the cardiac vessel in which the fixation mechanism 610 is positioned, thus fixing the lead 600 in the implanted position.

In one embodiment, once the fixation mechanism 610 is deployed, the tendon 640 may be maintained under tension and secured to the lead body 616 to retain the radially expandable structure 636, and thus the fixation mechanism 610, in the deployed, radially expanded configuration. The fixation mechanism 610 can further be returned to the radially collapsed configuration of FIG. 7A by releasing the tension in the tendon 640, thus permitting removal and/or repositioning of the lead 600. Alternatively, in other embodiments, the lead 600 may include one or more retention structures such as one or more deflectable stops 350 of the lead 300 described above, for preventing movement of the ring 630 in the distal direction once the fixation mechanism 610 is deployed. In other embodiments (not shown), other or additional structures are provided for retaining the fixation mechanism 610 in the deployed configuration of FIG. 7B. It is again emphasized that the illustrated structures and methods for retaining the fixation mechanisms in their deployed configurations are exemplary only.

In another embodiment, the ribs 636 are self-expanding and are retained in the radially collapsed configuration of FIG. 7A by, for example, a retention structure (not shown) preventing spontaneous proximal movement of the ring 630 but which can be disengaged by a sufficient proximally directed force applied to the tendon 640. Once the retention structure is disengaged, the ribs 636 can self-expand to the configuration of FIG. 7B. Both of the latter two embodiments advantageously allow the tension in the tendon 640 to be removed after deployment of the fixation structure 610.

Figure 7C:
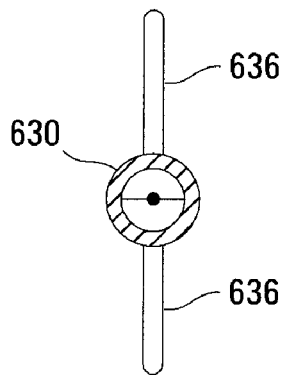

FIG. 7C is an end view of the lead 600 showing the ribs 636 in the radially expanded configuration for engaging the inner surface of the vessel (e.g., the branch vessel 34). It will be appreciated that although the lead 600 of FIGS. 7A-7C includes two radially expandable ribs 636 oriented approximately 180 degrees apart, in other embodiments, one or more than two ribs may be used. In one embodiment, the lead 600 includes a single radially expandable rib 636. In another embodiment, the lead 600 includes two ribs 636 oriented approximately 90 degrees apart. In such embodiments, the ribs 636 may be sized and oriented so as to bias the lead electrode into the target tissue (e.g., the myocardium). Other variations in the number and orientation of the ribs 636 will be apparent to those skilled in the art based on the foregoing.

Figure 8A:
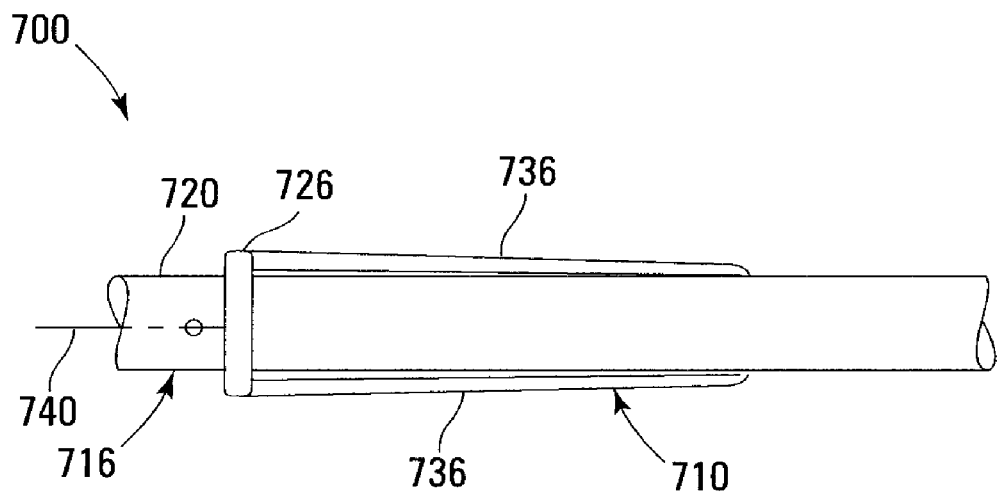
FIGS. 8A and 8B illustrate a distal region of a lead including a self-expanding fixation mechanism according to another embodiment of the present invention.
Figure 8B:
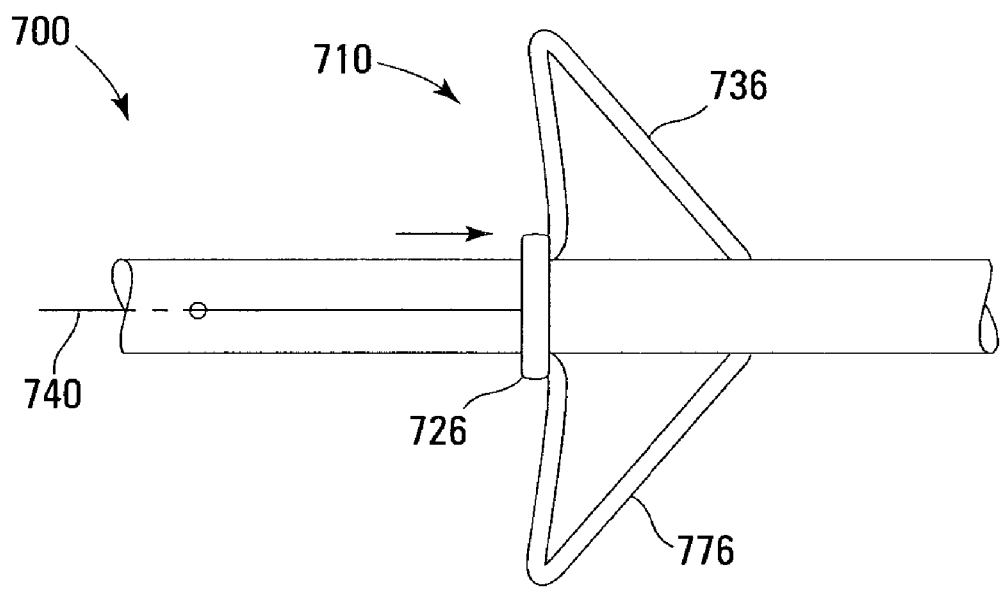

FIGS. 8A and 8B illustrate a portion of a distal region of a lead 700 including an alternative fixation feature, which as illustrated is a self-expanding fixation mechanism 710 according to another embodiment of the present invention. As shown in FIGS. 8A and 8B, the lead 700 includes a body 716 on which the fixation mechanism 710 is disposed. As further shown, the fixation mechanism 710 includes a proximal floating ring 726 and a plurality of radially self-expanding ribs 736 attached at opposite ends to the ring 726 and to the body 716. A tendon 740 is disposed within the body 716 (e.g., within a lumen, not shown) and attached to one or more locations on the ring 726. In the illustrated embodiment, a portion of the tendon 740 extends through an aperture 746 in the body 716 and along the outer surface 720 to the ring 726 to which it is attached. Other embodiments (not shown) may employ an alternative arrangement for attaching the tendon 740 to the ring 726.

A tensile force applied to the tendon 740 operates to pull the proximal ring 726 in the proximal direction to retain the self-expanding ribs 736 in the radially collapsed configuration of FIG. 7A for delivery of the lead 700. In one embodiment, the tendon 740 is secured, under tension, near the proximal end (not shown) of the lead 700. Once the lead 700 is delivered to the desired implantation location, the tension in the tendon 740 is released, and the self-expanding ribs 736 expand to their deployed configuration as illustrated in FIG. 8B.

In the illustrated embodiments, the ribs 636, 736 are shown disposed on the outside of the outer surface 620, 720 of the respective lead body when in the radially collapsed, undeployed configuration. In another embodiment (not shown), the ribs may be substantially flush with the respective outer surfaces when in the radially collapsed configuration, for example, by residing in slots formed in the lead body. Additionally, in some embodiments, the ribs may be formed integrally with the lead body. In other embodiments, the fixation mechanisms 610, 710 may be separate elements, with the ribs attached to an anchor (not shown) which is in turn attached to the lead body.

The ribs 636, 736 may, in some embodiments, be formed from any of the materials described above in connection with the fixation mechanisms 300, 400. In particular, in the self-expanding rib embodiments, the ribs are made at least partially from materials having desirable shape memory and superelastic properties such as, for example, Nitinol. In other embodiments, the ribs may be formed from the same materials used to form the lead body (e.g., polyurethane and/or silicone).

In some embodiments, the ribs 636, 736 may be configured to facilitate extraction of the leads, if desired. For example, in one embodiment, the ribs 636 and/or 736 may include a polymer membrane (not shown) made of an ingrowth resistant material (e.g., PTFE) to prevent or substantially impede tissue ingrowth in the space between the rib and the respective lead. In other embodiments, the ribs 636, 736 themselves may be made from a material, such as PTFE, that is resistant to tissue ingrowth. In some embodiments, the ribs 636, 736 may be made from resorbable materials, as are known in the art, to facilitate extraction even after extended periods of implantation.

Figure 9A:
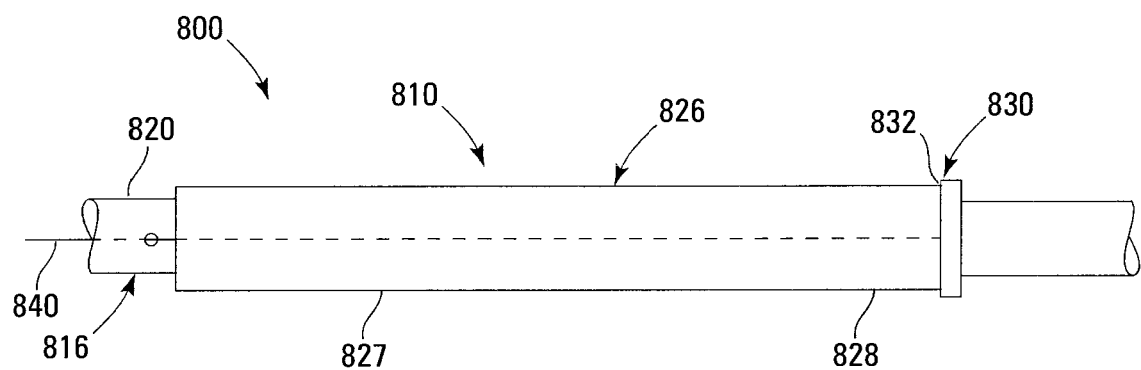
FIGS. 9A and 9B illustrate a distal region of a lead including an expandable fixation mechanism according to another embodiment of the present invention.
Figure 9B:
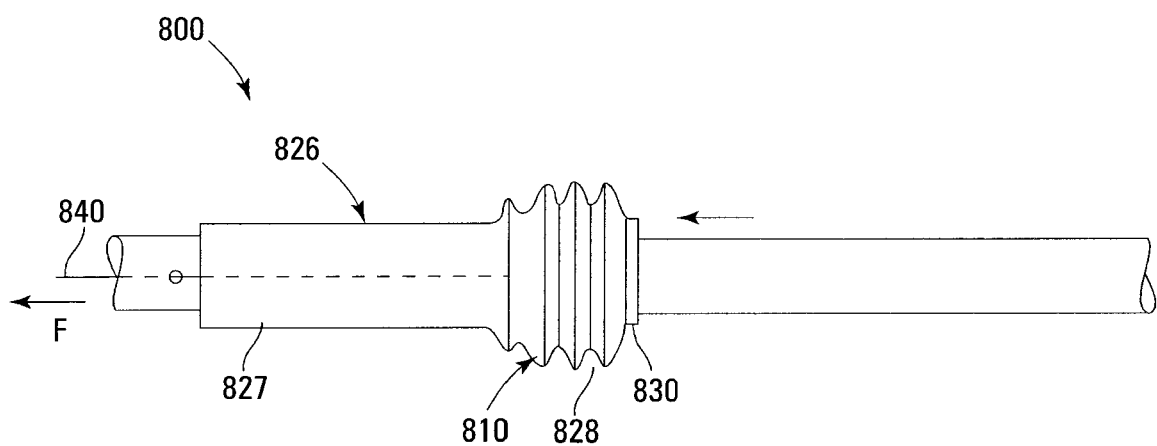

FIGS. 9A and 9B illustrate a portion of a distal region of a lead 800 including an alternative fixation feature, which as illustrated is a radially expandable fixation mechanism 810 according to another embodiment of the present invention. As shown in FIGS. 9A and 9B, the lead 800 includes a lead body 816 having an outer surface 820. The fixation mechanism 810 is disposed on the lead body 616 and includes a sheath 826 having a proximal portion 827, a distal portion 828, and a floating reinforcing ring 830 at a distal end 832. A tendon 840 is disposed partially within the body 816 (e.g., within a lumen, not shown) and attached to one or more locations on the distal ring 830 in substantially the same manner as described above in connection with, for example, the leads 300, 500 and 600. The proximal portion 827 of the sheath 826 is frictionally coupled to the outer surface 820 of the lead body 816. The reinforcing ring 830 is adapted to translate along the lead body 816.

In the illustrated embodiment, the sheath 826 is normally in the radially collapsed configuration as shown in FIG. 9A for delivery of the lead 800, and a tensile force is applied to the tendon 840 to pull the tendon 840 and the reinforcing ring 830 proximally relative to the lead body 816 to deploy the fixation mechanism 810. The frictional forces coupling the proximal portion 827 and the outer surface 820 prevent the proximal portion 827 from sliding proximally along the lead body 816 under the action of the tensile force on the tendon 840. The distal portion 828 of the sheath 826 is sufficiently flexible, however, such that as the reinforcing ring 830 is pulled proximally under the action of the tensile force on the tendon 840, the distal portion 828 will tend to bunch up and expand radially outward as shown in FIG. 9B to form a tissue engaging surface for lead fixation.

As with various embodiments described above, the tendon 840 may, in one embodiment, be secured to the lead body 816 under tension to maintain the sheath distal portion 828 in its deployed configuration shown in FIG. 9B. In other embodiments, the lead 800 may include structures, such as the retention structures described above, to prevent movement of the reinforcing ring 830 in the distal direction once the fixation mechanism 810 is deployed. As with the embodiments described above, any other structures or methods for retaining the fixation mechanism 810 in the deployed configuration of FIG. 9B may be used.

The sheath 826 may have any structure providing the desired flexibility. In one embodiment, the sheath 826 may be a braided tube which may or may not include a polymeric coating. In one embodiment, the sheath 826 may be a reinforced or an unreinforced polymer tube. In some embodiments, the sheath 826 may include a coating or layer of material that discourages or substantially prevents tissue ingrowth (e.g., PTFE).

The tendons of the various embodiments can have any structure capable of receiving and transmitting a static tensile load while providing the desired flexibility, and in the embodiments where the tendon is maintained under tension, having desired fatigue response characteristics. For example, the tendon may be in the form of a wire, cable, or thread. Suitable tendon materials include, without limitation, suture materials as are known in the art as well as other polymers and metals such as stainless steel or superelastic alloys such as Nitinol. The tendon may optionally be coated with a lubricious material to reduce frictional forces between the tendon and the inner wall of the respective lumen carrying the tendon.

Any or all of the fixation features described above may include additional features to enhance frictional engagement for acute and/or chronic fixation, as desired. By way of example only, such features include, surface roughening or other surface treatments to increase frictional engagement with the cardiac vessel tissue. Additionally, in some embodiments in which removability is desired, the fixation features may include polymer coatings or other features to discourage tissue ingrowth and facilitate removal and/or repositioning of the lead if desired.

It is emphasized that in some embodiments, the radially expandable fixation mechanisms do not extend completely circumferentially around the respective lead bodies. Additionally, the floating members (e.g., the ring 330 of the fixation mechanism 310) can have any structure adapted to permit translation along the lead body. For example, the floating member could be configured to ride in a slot in the lead body, and need not be configured as a ring as shown in the illustrated embodiments.

Thus, to fixate a portion of a cardiac lead in a target cardiac vessel using any of the deployable fixation features described above, the lead is first transvenously delivered to its implantation position with the fixation feature in its undeployed state. Such lead delivery can be accomplished according to any method and using any delivery device now known (e.g., guide catheters, guide wires) or later developed. Once the lead is delivered, the tendon (or in some embodiments, a plurality of tendons) can be actuated to deploy the fixation feature(s) and secure the lead in its implanted position.

In the embodiments in which a tensile force applied to the tendon causes the fixation feature to be deployed (e.g., the leads 50, 150, 250, 300, 500, 600, 800 described above), the lead may be held in place as the tensile force is applied to the tendon, so as to prevent the lead itself from being displaced under the action of the tensile force. By way of example only, for the lead 300 described above, the proximal end of the lead can be held in place while the tensile force is applied to the tendon 340 to expand the radially expandable structure 336. Once the fixation feature is deployed in frictional engagement with the respective cardiac vessel wall, the tendon can be secured to the lead, if necessary, to retain the fixation feature in its deployed configuration. Alternatively, in embodiments including other structures (e.g., the retention structures 350 of the lead 300) to retain the fixation feature in its deployed configuration, the tension in the tendon can be relieved after deployment, or the tendon can be removed from the lead altogether if desired.

In other embodiments utilizing a self-expanding fixation feature that is retained in its undeployed configuration by tension in the tendon (e.g., the leads 400, 700 above), the tension can be removed after the lead is delivered to its implantation position as described above. Removal of this tension thus activates the fixation feature and causes the fixation feature to frictionally engage the respective vessel wall. The tendon can be left in place within the lead, or if desired, can be removed (e.g., by cutting the tendon).

Figure 10A:
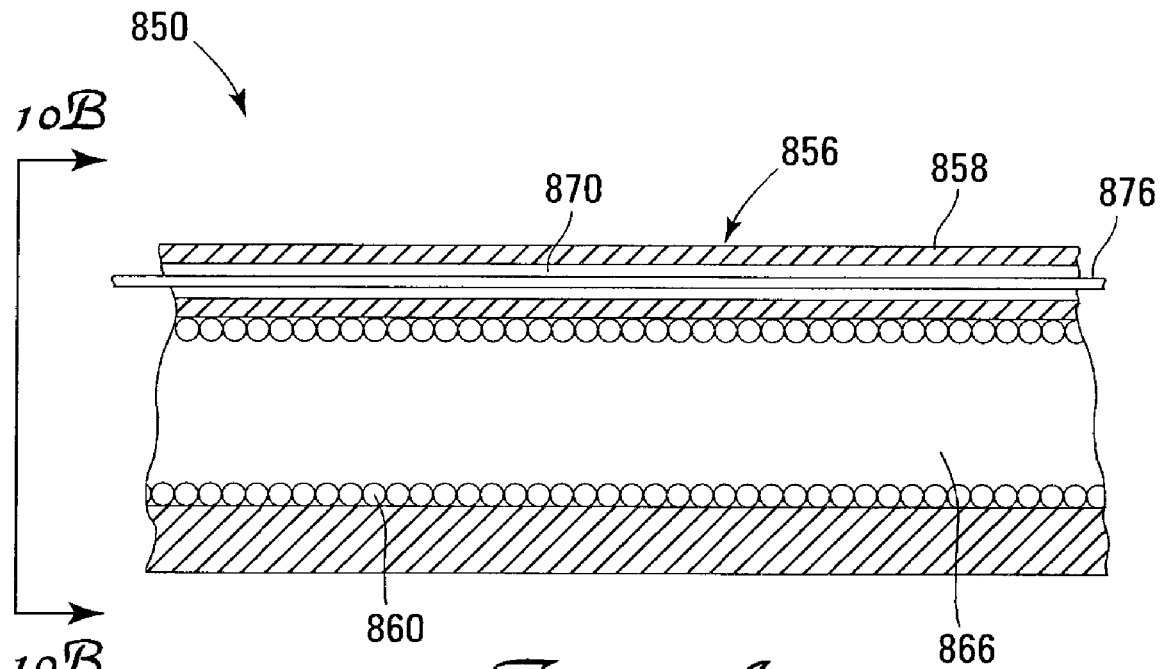
FIGS. 10A and 10B illustrate partial cross-sectional views of an alternative lead according to another embodiment of the present invention.
Figure 10B:
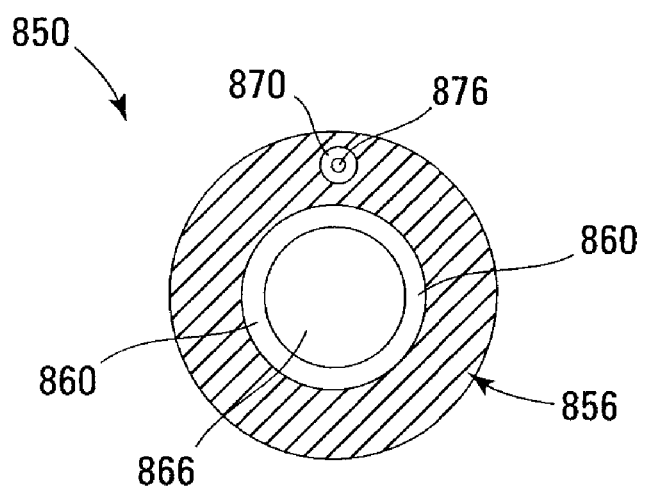

FIGS. 10A and 10B are partial cross-sectional views of a portion of a multi-lumen lead 850 adapted to include the various fixation features illustrated and described above. As shown in FIGS. 10A and 10B, the lead 850 includes a body 856 including an outer insulating sheath 858, and a conductor coil 860 covered by the insulating sheath 858 and defining a primary lumen 866. As further shown, a secondary lumen 870 is disposed within the insulating sheath 858 for carrying a tendon 876 adapted for use with any of the foregoing fixation features. Thus, in the illustrated embodiment, the tendon 876 for deploying the fixation feature (not shown) is not carried by the primary lumen 866. It is emphasized that the multi-lumen lead 850 can be used with any of the deployable fixation features illustrated herein and described above. Additionally, in some embodiments, more than one secondary lumen can be provided to accommodate additional tendons or for other purposes (e.g., drug delivery).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable system comprising:
   a pulse generator; and
   a lead having a proximal end coupled to the pulse generator, the lead configured to be partially implanted in a cardiac vessel and including:
      an elongate lead body defining a proximal region and a distal region and including an outer insulating sheath, the distal region including an electrode on the body, a deflection location on the body in which a portion of the outer insulating sheath has been removed to form the deflection location, and a deflectable region having a tissue-engaging outer surface; and
      a tendon disposed at least partially within the body and attached to the body under tension at a first attachment location distal to the deflectable region,
      wherein the lead is configured such that tension in the tendon maintains the deflectable region in a deflected shape in which the tissue-engaging outer surface can frictionally engage an inner wall of the cardiac vessel.

2. The lead of claim 1 wherein the distal region includes a plurality of deflection locations on the lead body, and wherein the deflectable region is adapted to deflect at each of the deflection locations.

3. The lead of claim 1 wherein the deflection location includes transition from a relatively stiff material to a relatively flexible material.

4. The lead of claim 3 wherein the relatively stiff material is polyurethane and the relatively flexible material is silicone.

5. The lead of claim 1 wherein the deflection location includes a transition from a first portion of the lead body having a first wall thickness to a second portion of the lead body having a second wall thickness, wherein the first wall thickness is greater than the second wall thickness.

6. The lead of claim 1 wherein the deflected shape is a J-shape.

7. The lead of claim 1 and further comprising a distal tip, wherein the first attachment location is next to the distal tip.

8. The lead of claim 1 further comprising a distal tip, wherein the first attachment location is proximal to the distal tip.

9. The lead of claim 1 wherein the deflected shape is an S-shape.

10. The lead of claim 1 wherein the distal region includes a plurality of deflection locations, and wherein the deflected shape is a sinusoidal shape.

11. The lead of claim 1 wherein the distal region includes a plurality of deflection locations offset from each other about a circumference of the lead body, and wherein the deflected shape includes a three-dimensional curve.

* * * * *